(12) United States Patent
Renucci

(10) Patent No.: US 10,039,768 B2
(45) Date of Patent: Aug. 7, 2018

(54) AXILLARY TRANSDERMAL COMPOUND DELIVERY SYSTEM

(71) Applicant: Michael Renucci, San Diego, CA (US)

(72) Inventor: Michael Renucci, San Diego, CA (US)

(73) Assignees: Michael Renucci, San Diego, CA (US); Lolly Christine Love, San Diego, CA (US)

( * ) Notice: Subject to any disclaimer, the term of this patent is extended or adjusted under 35 U.S.C. 154(b) by 0 days.

(21) Appl. No.: 14/957,487

(22) Filed: Dec. 2, 2015

(65) Prior Publication Data

US 2016/0310498 A1    Oct. 27, 2016

Related U.S. Application Data

(60) Provisional application No. 62/150,517, filed on Apr. 21, 2015.

(51) Int. Cl.

| | | |
|---|---|---|
| *A61K 31/522* | (2006.01) | |
| *A61Q 15/00* | (2006.01) | |
| *A61K 31/352* | (2006.01) | |
| *A61K 31/465* | (2006.01) | |
| *A61K 31/4188* | (2006.01) | |
| *A61K 31/14* | (2006.01) | |
| *A61K 33/34* | (2006.01) | |
| *A61K 33/18* | (2006.01) | |
| *A61K 33/04* | (2006.01) | |
| *A61K 8/02* | (2006.01) | |
| *A61K 9/06* | (2006.01) | |
| *A61K 9/00* | (2006.01) | |
| *A61K 47/10* | (2017.01) | |

(52) U.S. Cl.
CPC .......... *A61K 31/522* (2013.01); *A61K 8/0229* (2013.01); *A61K 9/0014* (2013.01); *A61K 9/06* (2013.01); *A61K 31/14* (2013.01); *A61K 31/352* (2013.01); *A61K 31/4188* (2013.01); *A61K 31/465* (2013.01); *A61K 33/04* (2013.01); *A61K 33/18* (2013.01); *A61K 33/34* (2013.01); *A61K 47/10* (2013.01); *A61Q 15/00* (2013.01); *A61K 2800/28* (2013.01); *A61K 2800/413* (2013.01); *A61K 2800/596* (2013.01); *A61K 2800/74* (2013.01)

(58) Field of Classification Search
CPC ...... A61K 9/06; A61K 31/352; A61K 31/465; A61K 33/04; A61K 2800/413; A61Q 15/00
See application file for complete search history.

(56) References Cited

U.S. PATENT DOCUMENTS

| | | | |
|---|---|---|---|
| 6,503,492 B2 * | 1/2003 | McGlone ................. | A61K 8/26 424/400 |
| 2010/0119461 A1 * | 5/2010 | Bicard-Benhamou . | A01N 59/16 424/49 |
| 2012/0107258 A1 * | 5/2012 | Kuhn ....................... | A61K 8/34 424/65 |

FOREIGN PATENT DOCUMENTS

EP         0260030 A2 *   3/1988

OTHER PUBLICATIONS

Okoro Uchechi et al.; Title: Nanotechnology and Nanomaterials "Application of Nanotechnology in Drug Delivery", book edited by Ali Demir Sezer, Chapter 6 Nanoparticles for Dermal and Transdermal Drug Delivery; Published Jul. 25, 2014.*

Trommer, et al; title: Overcoming the stratum corneum: The modulation of skin penetration; Skin Pharmacol Physiol.; vol. 19, pp. 106-121; published online May 9, 2006.*

* cited by examiner

*Primary Examiner* — Yanzhi Zhang
(74) *Attorney, Agent, or Firm* — Timothy Marc Shropshire; Eric Brandon Lovell; Garrett James O'Sullivan

(57) ABSTRACT

A deodorant stick drug delivery system has one or more hydrophilic carriers, water, one or more gelling agents, an active ingredient, and a solvent. The active ingredient may be cannabinoids, nicotine, caffeine, vitamins, insulin and tetrahydrocannabinol. The solvent may be, for example dimethyl sulfoxide, benzyl alcohol, and water. The solvent may be non-mutagenic, and/or non-teratogenic. Nanoparticles may be used that enable the active ingredient to pass through endothelial tissue, and microparticles may be used to create microabrasions in the skin and increase absorbancy. Finally, a permeability compound may be used to increase permeability across dermal layers.

18 Claims, No Drawings

AXILLARY TRANSDERMAL COMPOUND DELIVERY SYSTEM

CROSS-REFERENCE TO RELATED APPLICATION(S)

The present application claims priority to U.S. Provisional Patent Application No. 62/150,517 filed on Apr. 21, 2015, entitled "Underarm Transdermal Drug Delivery System" the entire disclosure of which is incorporated by reference herein.

BACKGROUND OF THE INVENTION

1. Field of Invention

The present invention relates to the field of transdermal compound delivery systems, in particular those systems in combination with underarm deodorant or antiperspirant.

2. Description of Related Art

Skin is comprised of dermal layers from the interior layer to exterior layer comprising the hypodermis, dermis, and epidermis. Each layer of skin is further comprises of blood vessels and cellular matrices having junctions between each cell. The external surface of the skin, or epidermis, has a plurality of pores that allow for selective permeability of substances into and out of the body. Specifically, the axillary region of the body comprises a high concentration of pores as well as lymph nodes and a plexus of blood vessels. The lymph nodes and blood vessels are integral components of the circulatory system, which is responsible for the transportation of compounds throughout the body to their targeted destination. This configuration in the axillary region of the body provides an ideal opportunity to introduce compounds into body systems.

However, the current state of the art has failed to establish an effective and efficient combination transdermal delivery system for desired compounds and deodorant/antiperspirant. Adhesive patches are commonly known for administering nicotine or birth control. These patches require a surface that is dry and relatively free of hair to promote adhesion. Furthermore, the adhesive compounds often contain irritants resulting in adverse effects on the user. Testosterone has been known to be applied via transdermal processes, but has been directed against being combined with a deodorant or antiperspirant. Other systems will actually perforate the skin through micro-abrasion or microinjections to introduce compounds, which may leave the user susceptible to infection.

A large majority of the global population currently utilizes some form of deodorant/antiperspirant as a part of their daily hygiene routines. Although the application of deodorant/antiperspirant has been common practice and would rarely be forgotten, an overwhelming number of people will neglect to take necessary medications. Outside of medicinal applications, a combination of compounds with deodorant sticks could provide outstanding efficiency and efficacy for the consumption of recreational and supplemental compounds.

Based on the foregoing, there is a need in the art for a transdermal delivery system that combines the desired compound, to be introduced into the body, with the routine daily use of a deodorant/antiperspirant.

SUMMARY OF THE INVENTION

A deodorant stick drug delivery system has one or more hydrophilic carriers, water, one or more gelling agents, an active ingredient, and a solvent. The active ingredient may be cannabinoids, nicotine, caffeine, vitamins, insulin and tetrahydrocannabinol.

The solvent may be, for example dimethyl sulfoxide, benzyl alcohol, and water. The solvent may be non-mutagenic, and/or non-teratogenic. Nanoparticles may be used that enable the active ingredient to pass through endothelial tissue, and microparticles may be used to create microabrasions in the skin and increase absobancy. Finally, a permeability compound may be used to increase permeability across dermal layers.

The foregoing, and other features and advantages of the invention, will be apparent from the following, more particular description of the preferred embodiments of the invention, the accompanying drawings, and the claims.

BRIEF DESCRIPTION OF THE DRAWINGS

Not applicable

DETAILED DESCRIPTION OF PREFERRED EMBODIMENTS

Preferred embodiments of the present invention and their advantages may be understood by the follow detailed description.

A deodorant or antiperspirant stick is used daily by the majority of the developed world, and the desire not to offend others leads people to use them at least once a day, typically after a shower in the morning, to prevent the emission of unpleasant odor and a malodorous reputation with peers. Use of the deodorant stick as a drug delivery system has the advantage that it is rarely forgotten due to social coercive forces, whereas medications are often forgotten as they are a largely private consumption and do not have an inherent reminder, such as the social queues associated with deodorant and antiperspirant use. In addition, the use of a deodorant has become a learned behavior through many years of repeated use for people.

The composition of the skin in the axillary region has a considerably higher absorption rate than other areas of the skin. The absorption rate is defined by the quantity of transmission of a substance across the dermal barrier over a period of time. This high absorption rate makes the axilla a desirable site for a transdermal compound delivery system.

Deodorants are classified as cosmetics by the FDA and are designed to eliminate odor. Frequently they are alcohol-based, and may contain other anti-microbials such as triclosan, or metal chelants to slow bacterial growth. Deodorants and antiperspirants come in gels or sticks, and in sprays or creams.

In an embodiment, a transdermal delivery system include at least one phase where desired compounds are dissolved in a solvent such as dimethyl sulfoxide (DMSO), benzyl alcohol, water, or another solvent appropriate for human consumption. These solvents are used to dissolve compounds such as cannabinoids (CBDs), nicotine, caffeine, vitamins, Tetrahydrocannabinol (THC), vitamins, insulin, and other medications or compounds taken regularly. Once the desired compound is identified, a corresponding solvent is selected based on the compound. For example, vitamin C is generally water soluble. Once the compound is in an aqueous mixture is can be combined with the components of the deodorant or antiperspirant.

In an embodiment, the solvents used are non-mutagenic and non-teratogenic.

In an alternative embodiment, the transdermal delivery system is comprised of nanoparticles that are coated in the dissolved desired compound. The nanoparticles are configured to enter the body through the layers of dermis due to their size. The nanoparticle is capable of passing between endothelial tissues where they are then able to enter the circulatory system through various blood vessels. The dissolved compound on the surface of the nanoparticle is then introduced to target areas of the body including the musculature, various organs, and the circulatory system itself, if the desired effect of the compound involves vasodilation or vasoconstriction. The nanoparticles may dissolve in the plasma as be excreted through known biological processes.

In an embodiment, the transdermal delivery system comprises micro particles capable of creating microabrasions in the skin to improve the delivery of desired compounds by microperforations in the dermis allowing direct introduction of the compounds into the body.

In an embodiment, compounds are added to the deodorant or antiperspirant to promote permeability across the dermal layers. Examples of these compounds are isopropyl alcohol and acetone. Other compounds may be used based on their ability to increase permeability and acceptability for human consumption.

The gels, sticks, sprays, and creams are comprised of various active and inactive components based on the desired effect of the deodorant or antiperspirant. The manufacturing process of these compounds is generally known and understood in the art.

Deodorant sticks having active ingredients therein, such as nicotine, caffeine, vitamins, THC, or CBDs, may comprise the following ingredients (listed with percentages for illustrative purposes):
Hydrophilic Carriers: 50-80%
Water: 15-20%
Active Ingredient (Nicotine, Caffeine, Vitamins or THC): 0.04-20%
Gelling Agents (Gellants): 5-8%
Clarifying Agents/Solubilizers: 0-6%
Antimicrobial Agents: 0-2%
Fragrance (Parfum): 0-2%
Chelating Agents (Chelants): 0-0.1%
Neutralizing Agent 0-0.01%
Anti-oxidants 0-0.01%
Colorants 0-0.001%

In order to achieve this, the ingredients, including the active ingredient(s) are mixed and gelled before being inserted into deodorant sticks, sprays or creams. Smaller percentages of active ingredients do not require a significant adjustment of hydrophilic carriers and water, however larger amounts (over 5% of the bar) do, in order to maintain the consistency of the deodorant or antiperspirant for application.

In an embodiment, the primary carrier system for deodorant sticks today usually consists of one or more glycols, such as Propylene Glycol and/or Dipropylene Glycol, with a selected amount of water (aqua). This primary carrier system is gelled using Sodium Stearate. It is preferred for optimizing the clarity of the sticks. In glycol-based sticks, the composition is further adapted to achieve the desired esthetics and gelling properties. The result is a "Sodium Stearate" that contains appreciable amounts of Sodium Palmitate, Sodium Stearate, Sodium Arachidate and Sodium Behenate. The sticks that result usually aren't as clear, but they provide superior set point and payoff characteristics.

In an embodiment, clarifiers and/or solubilizers may be used to promote stick clarity and reduce the potential for syneresis, particularly when high levels of fragrance are utilized. Nonionic surfactants of moderate to high hydrophilic-lipophilic balance (HLB), such as PPG-3 Myristyl Ether or Isosteareth-20, may be utilized. Antimicrobials are sometimes added to inhibit the growth of microorganisms in the armpits. This can help with the reduction of axillary malodor since certain bacteria metabolize sweat and sebum into volatile, malodorous substances. Triclosan remains the most commonly used antimicrobial, although continuing bad press has resulted in its removal from some products and the adoption of alternatives including specially selected botanical extracts and silver chloride.

In an embodiment, fragrance (parfum) is frequently used in deodorants and, in the absence of antimicrobials or fragrant and/or antimicrobial essential oils, it is solely responsible for the "deodorizing" effect of the product. The base used by the perfume house for a deodorant stick fragrance oil is likely to differ appreciably from that used for emulsion-based products since there is no oil phase in which to dissolve the fragrance oil. Hence, it is likely to be more polar. In an alternative embodiment, fragrances are excluded from the deodorant or antiperspirant.

In an embodiment, chelating Agents, such as Disodium EDTA or Tetrasodium EDTA, may be used to tie up multivalent ions that become part of the composition, particularly through the water supply, but also through aqueous or glycolic extracts. Many of these ions can promote the oxidation of unsaturated ingredients (substances with carbon-carbon double bonds). By making the metal ions inactive, the chelants enhance fragrance stability and so extend product shelf life.

In an embodiment, neutralizing agents are occasionally added to improve stick clarity and/or ensure that the desired pH for the deodorant stick (typically about 9) is met. The Sodium Stearate sold as gellants for deodorant sticks typically has a small amount of free fatty acid present. This limits the alkalinity of the deodorant stick, but it can also result in a haze from the free acid. Alkalis that may be used to neutralize the free fatty acid include Aminomethyl Propanol, Poloxamine 1307, Sodium Hydroxide and even Tetrasodium EDTA.

In an embodiment, an anti-oxidant, most commonly BHT, may be added as an alternative or as a supplement to the stabilizing effects of chelants. Again, the intent is to extend shelf life by reducing oxidative processes.

In an embodiment, antioxidants may be included for their beneficial health effects. Anti-oxidants are capable of binding and rendering free radicals ineffective. The antioxidants would be dissolved, where appropriate, by a solvent and then include in the manufacturing the deodorant.

In an embodiment, various components may be added to the deodorant stick for aesthetic purposes. Colorants may be added at very low level for their esthetic benefits. The use levels of these water or alcohol soluble dyes are so low that skin and fabric staining are rarely a legitimate concern.

In an embodiment, a 100 gram (3.49 oz.) deodorant stick lasts an average person 30 days when applied twice a day, which results in a typical application of 1.67 g, or 1670 mg, across both armpits. Often, deodorant is used two or more times per day. For deodorant sprays, the quantity per application is similar, but differs depending on the user.

In an embodiment, the use of a deodorant stick to deliver caffeine is novel and beneficial in that it saves the user time and energy in the morning. As something he necessarily does every day, applying deodorant with caffeine saves the time in making and drinking coffee to receive the morning jolt. Caffeine is added to the deodorant in the proportion of approximately 12%, to provide approximately 100 mg of caffeine per application, which is similar to a cup of coffee. The amount of caffeine in the deodorant may be varied to provide between 20 mg and 60 mg per application of the deodorant. Cups of coffee can range between 50 and 450 mg of caffeine, and the deodorants would vary in the amount of caffeine delivered. The deodorant may be coffee-scented and may have names derived from the location of famed coffee plants. The deodorant would retain its consistency for application by varying the water and hydrophilic carriers to permit the same consistency despite an increase in dry powder within the mixture. Where absorption rates from the underarm result in less than the full dosage being absorbed, greater amounts of caffeine may be added.

In an embodiment, the use of a deodorant stick to deliver vitamins is also novel. Vitamins may be present in the deodorant in the amount of a daily dosage of the vitamin, or half a recommended dose based on the assumption of a twice-daily application. The amounts for typical vitamins are as follows:

Biotin (a.k.a. Vitamin B7 or Vitamin H): Like the rest of the water-soluble B-complex vitamins, biotin plays a role in cell growth and food metabolism. RDA: 30 mcg; Choline: Choline, another water-soluble B vitamin, is a building block of the neurotransmitter acetylcholine, which is essential for the nerve and brain activities that control memory and muscle movement. RDA: 550 mg; Copper: Important in the creation of red blood cells, copper is also important for proper energy metabolism, immunity, and nervous system function. RDA: 900 mcg; Folic Acid (a.k.a. folate or folacin): Folic acid is vital for pregnant women to ensure the baby's proper development, helping prevent birth defects in the brain and spine. RDA: 400 mcg; Iodine: This essential trace mineral is a crucial component of thyroid hormones, which maintain our basal metabolic rate (BMR). Iodine also helps to regulate body temperature, nerve and muscle function, and plays a role in the body's growth and development. RDA: 150 mcg; Iron: Iron helps hemoglobin, a component of red blood cells, and myoglobin (hemoglobin's counterpart in muscles) bring oxygen to all the cells that need it. Iron is also important in the production of amino acids, collagen, neurotransmitters, and hormones. RDA: 8 mg; Magnesium: Magnesium is a macromineral that partners with calcium to assist with proper muscle contraction, blood clotting, cell signaling, energy metabolism, blood pressure regulation, and building healthy bones and teeth. RDA: 400 mg; Molybdenum: RDA: 45 mcg; Niacin (a.k.a. Vitamin B3 or Nicotinic Acid): RDA: Men=16 mg; Women=14 mg; Pantothenic Acid (a.k.a. Vitamin B5): RDA: 5 mg (AI); Riboflavin (Vitamin B2): RDA: Men=1.3 mg; Women=1.1 mg; Selenium: RDA: 55 mcg; Thiamin (a.k.a. Vitamin B1): RDA: Men=1.2 mg; Women=1.1 mg; Vitamin A (a.k.a. retinol, retinal, retinoic acid): RDA: Men=900 mcg; Women=700 mcg; Vitamin B6 (a.k.a. pyridoxal, pyridoxine, pyridoxamine): RDA: 1.3 mg; Vitamin B12: RDA: 2.4 mcg; Vitamin C (a.k.a. asorbic acid): RDA: Men=90 mg; Women=75 mg (Smokers should add 35 mg); Vitamin D: RDA: 15 mcg; Vitamin E: RDA: 15 mg; Vitamin K: RDA: Men=120 mcg; Women=90 mcg (AI); Zinc: RDA: Men=11 mg; Women=8 mg.

The vitamins listed above are an exemplary list for illustrative purposes. The particular vitamin, amount by percent weight, and recommended use would extend to any vitamin beneficial to human growth and development.

These may be varied depending on the recommended dose, the absorption characteristics of the vitamin through the underarm, and the effect of the vitamin on the consistency of the underarm deodorant.

In an embodiment, the deodorant or antiperspirant may also be used for administering nicotine as a substitute or in conjunction with the use of patches. Nicotine in the amount of 7 mg to 21 mg per application would result from a nicotine concentration of 0.41%-1.25% in the deodorant bar, and would deliver an active dose once or twice a day, to assist in reducing cravings, for example, for a person who is trying to quit.

In an embodiment, the deodorant or antiperspirant may also contain THC where permitted by law, either for medicinal or recreation purposes, in the amount of approximately 12 mg per dose, or 0.71% of the ingredients of the deodorant. Where the dose is adjustable per desired application, the content of THC can be adjusted accordingly.

In an embodiment, the deodorant or antiperspirant contains insulin. Insulin is a known required medication for treatment of patients with Type I Diabetes Miletus, who are dependent on insulin, or Type II Diabetes Miletus, who may eventually require insulin. Rather than require painful injections, the insulin is dissolved, or liquid insulin is used directly.

The invention has been described herein using specific embodiments for the purposes of illustration only. It will be readily apparent to one of ordinary skill in the art, however, that the principles of the invention can be embodied in other ways. Therefore, the invention should not be regarded as being limited in scope to the specific embodiments disclosed herein, but instead as being fully commensurate in scope with the following claims.

I claim:
1. A deodorant stick drug delivery system consisting of:
   a. hydrophilic carriers;
   b. water;
   c. gelling agents;
   d. active ingredients, wherein the active ingredients are tetrahydrocannabinol, caffeine, and a plurality of vitamins;
   e. a solvent;
   f. microparticles; and
   g. a permeability compound configured to increase permeability across dermal layers.
2. The deodorant stick of claim 1, wherein the solvent is selected from the group consisting of dimethyl sulfoxide, benzyl alcohol, and water.
3. The deodorant stick of claim 2, wherein the solvent is non-mutagenic.
4. The deodorant stick of claim 3, wherein the solvent is non-teratogenic.
5. The deodorant stick of claim 4, wherein the microparticles create microabrasions.
6. The deodorant stick of claim 5, wherein the active ingredients are adapted to be transmitted across a dermal barrier.
7. A deodorant stick drug delivery system consisting of:
   a. hydrophilic carriers;
   b. water;
   c. gelling agents;
   d. active ingredients, wherein the-active ingredients are tetrahydrocannabinol, insulin, caffeine, and a plurality of vitamins;
   e. a solvent;
   f. microparticles; and
   g. a permeability compound configured to increase permeability across dermal layers, wherein the one or more active ingredients are adapted to be transmitted across a dermal barrier.

8. The deodorant stick of claim 7, wherein the solvent is selected from the group consisting of dimethyl sulfoxide, benzyl alcohol, and water.

9. The deodorant stick of claim 7, wherein the solvent is non-mutagenic.

10. The deodorant stick of claim 7, wherein the solvent is non-teratogenic.

11. The deodorant stick of claim 7, wherein the microparticles create microabrasions.

12. The deodorant stick of claim 7, wherein the active ingredients are adapted to be transmitted across a dermal barrier.

13. A deodorant stick drug delivery system consisting of:
   a. hydrophilic carriers;
   b. water;
   c. gelling agents;
   d. active ingredients, wherein the active ingredients are tetrahydrocannabinol, nicotine, caffeine, and a plurality of vitamins;
   e. a solvent;
   f. microparticles; and
   g. a permeability compound configured to increase permeability across dermal layers.

14. The deodorant stick of claim 13, wherein the solvent is selected from the group consisting of dimethyl sulfoxide, benzyl alcohol, and water.

15. The deodorant stick of claim 13, wherein the solvent is non-mutagenic.

16. The deodorant stick of claim 13, wherein the solvent is non-teratogenic.

17. The deodorant stick of claim 13, wherein the microparticles create microabrasions.

18. The deodorant stick of claim 13, wherein the active ingredients are adapted to be transmitted across a dermal barrier.

* * * * *